METHOD OF PRODUCING DIALKYL- AND TRIALKYL-SUBSTITUTED BENZALDEHYDES

FIELD OF THE INVENTION

This invention relates to a process for preparing specific substituted benzaldehydes through the reaction of substituted benzenes with carbon monoxide and aluminum chloride at a relatively low pressure, at a low temperature, and in the presence of at most a catalytic amount of an acid (such as aqueous hydrochloric acid). The resultant substituted benzaldehydes are useful as precursors to the formation of a number of different compounds, such as dyestuffs, flavorings, fragrances, nucleating agents, polymer additives, and the like. The inventive method provides a very cost-effective and safe procedure for producing such substituted benzaldehydes at very high yields.

BACKGROUND OF THE PRIOR ART

All U.S. Patent documents and other publication discussed below are herein entirely incorporated by reference.

Techniques for producing substituted benzaldehydes have been practiced for over a century. The primary method followed to formylate substituted benzene was the Gattermann-Koch reaction, developed in 1897. This reaction required the combination of equivalent amounts of aluminum chloride, carbon monoxide, and gaseous hydrogen chloride reacted in the presence of a substituted benzene. The temperature was controlled from 25 to 50° C., and the pressure was kept at 1,000 psig. Such a reaction yielded about 70% of the desired substituted benzaldehyde; however, the utilization of gaseous HCl and the need for high reaction pressures are highly undesirable from a safety standpoint. Furthermore, with the rising costs associated with the production of such substituted benzaldehydes, a 70% yield is unacceptable.

Modifications of the Gattermann-Koch reaction have been developed for specific monoalkyl-substituted benzaldehydes, such as in U.S. Pat. No. 4,622,429 to Blank et al.; however, these modifications do not produce significant amounts of dialkyl- or trialkyl-substituted compounds. In fact, patentees only concern with dialkyl- or trialkyl-substituted compounds are in their inherent production within reactions of monoalkyl-substituted benzenes in these modified Gattermann-Koch processes. There is no teaching nor fair suggestion that any further modifications of patentees' procedures when utilized with di- or tri-substituted compounds would produce extremely high yields of the pure corresponding benzaldehydes. Furthermore, Blank et al.'s methods only produce, at the high end, yields up to 77% for monoalkyl-substituted benzaldehydes.

Another method for formylating alkylated benzenes has been disclosed within U.S. Pat. No. 4,195,040 to Renner. Such a teaching includes the formylation of di- and tri-alkylbenzenes; however, this reference also requires the presence and use of large amounts of hydrochloric acid as well as non-raw material solvents (such as halogenated toluene). Such methods are thus highly undesirable since HCl is preferably avoided as a reactant in industrial scale manufacturing and the utilization of solvents other than those benzenes to be formylated requires further distillations which incur potentially large costs and hazardous process steps. In particular, halogenated solvents are avoided in large-scale reactions due to safety and environmental concerns.

Another more recent method utilizes an $HF-BF_3$ medium in which to react substituted benzenes systems with carbon monoxide to formylate such compounds. This method has produced very good yields of the dialkyl-substituted benzaldehydes; however, the $HF-BF_3$ catalyst presents a significant safety hazard which ultimately adds to the cost of the final product.

Thus, there exists a need to develop a proper formylation reaction for dialkyl- or trialkyl-substituted benzenes which produces high yields, does not require the utilization of large amounts of potentially dangerous HCl (or other acid) and other catalysts (and thus is relatively safe to perform), does not require the presence of solvents other than those which are raw materials within the procedure itself (i.e., allows for a neat reaction), and is highly cost-effective. To date, the prior art has not accorded such an improved di- and/or tri-alkyl substituted benzene formylation procedure.

OBJECTS OF THE INVENTION

Therefore, an object of the invention is to provide a process for producing high yields of dialkyl- or trialkyl-substituted benzaldehydes. A further object of the invention is to provide a highly cost-effective manner of producing such benzaldehydes which heretofore could not be produced in high yields without incurring potential problems from a safety perspective, particularly in a large-scale procedure. Another object of the invention is to provide a method of producing dialkyl- and trialkyl-substituted benzaldehydes in which little or no monoalkyl-substituted compounds are formed simultaneously and thus distillation from any reaction solvents does not prove problematic in isolating the target benzaldehyde. Additionally, it is an object of this invention to provide a method of producing specific di- and tri-alkylated benzaldehydes which requires, if at all, only a very low amount HCl (aqueous, dry, or gaseous) in order to effectuate the necessary formylation procedure.

DETAILED DESCRIPTION OF THE INVENTION

Accordingly, this invention encompasses a method of producing a benzaldehyde of the formula (I)

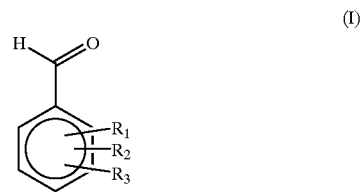

wherein $R^1$, $R^2$, and $R^3$ are the same or different and represent hydrogen and $C_1-C_4$ alkyl; and wherein at most one of $R^1$, $R^2$, and $R^3$ is hydrogen; which method is a neat procedure and comprises contacting a substituted benzene of the formula (II)

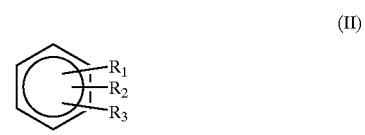

wherein $R^1$, $R^2$, and $R^3$ are the same or different and represent hydrogen and $C_1-C_4$ alkyl; and wherein at most one of $R^1$, $R^2$, and $R^3$ is hydrogen, in a carbon monoxide atmosphere having a pressure from about 20 to 200 psig, all in the presence of a metal halide and an acid selected from the group consisting of HCl, HBr, HF, HI, and mixtures thereof;

wherein the acid is present in a catalytic amount of from about 0.005 to about 0.01 moles per moles of the metal halide; and wherein the reaction temperature is from about −20° C. to about 25° C.

Any $C_1$–$C_4$ dialkyl- or trialkyl-substituted benzene may be introduced within the inventive method. Specific compounds include, as merely examples o-xylene, p-xylene, m-xylene, p-diethylbenzene, o-diethylbenzene, m-diethylbenzene, 1,2,3-trimethylbenzene, 1,2,4-trimethylbenzene, 1,2,5-trimethylbenzene, and 1,3,5-trimethylbenzene. These benzene compounds do not include halogen groups nor do they comprise fused ring systems, such as tetralin and/or indan.

The metal halide is preferably aluminum chloride, although other such halides may be utilized, such as aluminum bromide, iron (III) chloride, copper (II) chloride, zinc chloride, zirconium chloride, zirconium bromide, and the like. Also, partially hydrated metal halides may be utilized as these may produce hydrochloric acid upon dissociation within the reaction vessel, thereby providing the necessary acid component (for instance $AlCl_3 \cdot XH_2O$, wherein X is at most 1, preferably lower than 0.5, and most preferably between 0.01 and 0.1). This dissociation actually produces a requisite small, catalytic amount of aqueous hydrochloric acid without having to introduce potentially hazardous aqueous hydrochloric acid into the reaction (although such an outside addition is also an available and preferred alternative). In the past variations of the Gattermann-Koch process, it was theorized that the metal halide reacted with hydrogen chloride and carbon monoxide (all in equivalent amounts) to produce a formyl cation complex which had the capability of attacking electrophilically the aromatic system. After washing with water, the metal halide was removed leaving the formylated benzene derivative. In this invention, hydrogen chloride is used, if at all, in only a minuscule catalytic amount (from about 0.005 to about 0.01 moles per mole of metal halide). The metal halide is preferably present in a stoichiometric molar ratio as compared with the di- or tri-alkyl substituted benzene from about 1:2 to about 1:6, preferably from 1:3 to about 1:5, and most preferably at a ratio of about 1:4. Without intending to be bound to any specific scientific theory, it is believed that such a small catalytic amount of acid (such as selected from the group consisting of HCl, HBr, HF, HI, and mixtures thereof) coupled with the metal halide produces a certain "driving amount" of the formyl cation complex. This "driving amount" thus appears to shut down the rate of possible side product formation (i.e., dimerization or polymerization, as merely examples) which have been found to occur upon utilization of standard and much larger amounts of HCl (gaseous, in particular) in past methods. Thus, it has been determined that this catalytic amount of aqueous HCl provides the necessary reaction which ultimately forms very pure high yields of the target di- and/or tri-alkyl benzaldehydes.

Furthermore, the utilization of catalytic amounts of acid is, surprisingly, highly critical to the ultimate formation of the desired substituted benzaldehydes. As noted above, it had been presumed that larger stoichiometric amounts of (gaseous) hydrogen chloride were necessary to form the electrophilically attacking formyl cation complex with the metal halide and the carbon monoxide as the actual reactant. It has now been found that gaseous HCl is unnecessary to produce the desired benzaldehyde (although the gaseous form is still possible in this inventive method). Also, it has been discovered that only very small catalytic amounts (as defined above) of (preferably) aqueous hydrochloric acid unexpectedly are required to form the beneficial formyl cation complex reactant in order to produce the desired substantially pure substituted benzaldehydes in high yields (although gaseous and dry forms of HCl also work). From a safety and convenience perspective, aqueous hydrochloric acid is the preferred form for this inventive method. Gaseous HCl poses a potential health hazard since control of such a gseous state is rather difficult at times. Dry hydrochloric acid is more difficult to handle than the liquid form. Again, however, the hydrochloric acid may be added in any form, only preferably in aqueous solution.

As discussed above, it is important to note that this preferred aqueous HCl component may either be added into the overall reaction or may be generated simply upon dissociation of the metal halide in its hydrated form. Any molarity hydrochloric acid may be used, preferably the molarity is from about 0.01 to about 12, more preferably from about 10 to 12, and most preferably about 10 (concentrated), as long as the catalytic amount (in moles) in comparison to the metal halide is met and care is taken in handling such potentially corrosive material. Without the presence of any hydrochloric acid (either aqueous, dry, or gaseous), the yield of substituted benzaldehyde is reduced; when too much hydrochloric acid is present, the reaction either generates different isomers, dimers, and/or polymers of the benzaldehyde (and thus reduces the yield and detrimentally reduces the purity of the final reaction product) or results in a reaction which produces a sludge-like solid. One further benefit to utilizing aqueous HCl with the metal halide (in particular aluminum chloride), is that, upon completion of the formylation reaction, the remaining aluminum chloride exhibits a relatively neutral pH level. Such a product cannot be used again in this process; however, such neutralized aluminum chloride can be resold for other uses (such as flocculants, anti-perspirant components, etc.). Such recycling and reuse of compounds thus provides an environmentally friendly procedure which reduces the amount of waste needed to be removed from the manufacturing locations.

The carbon monoxide is introduced at a pressure of between about 20 and 200 psig, preferably from about 50 to about 110 psig, and most preferably at a pressure of about 90 psig. In the past, higher pressures (i.e., 200–600 psig) have been most readily utilized in such Gattermann-Koch modification reactions since it has been generally followed and understood that higher pressures result in faster reaction times (which, in turn, theoretically reduces costs in the long run). It has now been realized that the presence of alkyl groups on compounds which are subjected to high reaction pressures results in the production of various isomers, dimers, and the like, due to the highly reactive conditions such high pressures provide. Surprisingly, and counter to accepted practice, the inventive method of producing high yields of pure di- and trialkyl substituted benzaldehydes requires a relatively low reaction pressure at which the carbon monoxide reactant is introduced within the reaction. Furthermore, lower pressures are highly desirable from a safety perspective (particularly with such potentially harmful compounds as carbon monoxide) and are much easier to handle within a large-scale manufacturing process. Standard, and thus readily available, reactors utilized in such large-scale manufacturing procedures are able to withstand pressures of at most 100 psi. Through the utilization of the low pressures associated with the preferred embodiment of the inventive method, costs can be reduced through the availability to utilize such standard reactors. Thus, the inventive method is cost efficient which translates into lower costs to the end user of the target substituted benzaldehydes.

It has also been found that the yield of the target substituted benzaldehyde compounds, when using HCl (preferably aqueous hydrochloric acid) in catalytic amounts, is at its peak when the reaction temperature is optimized to about 0° C. (~95% yield of the target substituted benzaldehyde). A range of from about −10 to about 25° C., preferably from about −5 to about 5° C., and, again, most preferably about 0° C., should be followed. When the aqueous HCl is not added by hand (and thus is present due to the dissociation of the hydrated metal halide), the temperature must, surprisingly, be raised to about 25° C. in order to optimize the yield (again, about 70%). Since a higher temperature is expected to result in quicker reaction times, and thus possible higher yields, the necessity for utilizing a controlled system with a very low reaction temperature is very surprising, particularly since the yields have improved to levels unforeseen within modified Gattermann-Koch procedures. Furthermore, the utilization of such low temperatures is beneficial from both safety and cost perspectives. It is well known that the reactivity (and thus corrosiveness) of chlorides increases in relation to temperature, a reaction temperature of about 0° C., for example, will not corrode the reaction vessel at the same rate if a temperature of 50° C. or higher were followed (in fact, the higher temperature would theoretically result in a chloride being 32 times more reactive than the lower temperature listed above). Thus, the manufacturing life-span of reaction vessels can be extended with the utilization of low temperatures and the handling of such materials is improved.

An additional benefit from the inventive process lies in the lack of necessity of adding any solvents other than the raw materials. Thus, upon reaction of o-xylene (as merely an example), the only solvent present is that xylene isomer itself. No potentially hazardous halogenated solvents or other organic liquids are required to carry out such a reaction. As a result, the final product is generally a substantially pure liquid containing all of the same compound. There is no need to undertake time-consuming and costly distillation steps to purify the resultant compounds produced by this preferred inventive method. The term "neat procedure" is herein intended and defined as this aspect. Therefore, the only solvents utilized in a neat procedure are those which are raw materials within the inventive process itself.

PREFERRED EMBODIMENTS OF THE INVENTION

Examples of the particularly preferred inventive methods are outlined below.

EXAMPLE 1

204.90 g of aluminum chloride (mol. wt. 133.34; 1537 mmol) and about 817.08 g of o-xylene (mol. wt. 106.17; 7696 mmol) were charged to a 2 liter Paar®-brand stainless steel reaction vessel. To this mixture was added 5 drops of concentrated HCl. The vessel was sealed, purged three times with carbon monoxide with the pressure of the vessel increased to 90 psi for each purging. After the third time, the vessel was vented and a final introduction of CO was made at a pressure again of about 90 psi, the pressure at which the reaction was maintained for the total reaction time of about 14 hours (the reaction temperature was maintained at −3° C. for the duration as well). Once the reaction was complete, the resultant mixture was poured into about 500 mL of ice water to produce about 900 mL of a two-phase mixture. The top, organic layer was removed and washed three times with water using a separatory funnel and dried over magnesium sulfate. The residual organic phase was then decolorized with activated charcoal and subsequently distilled under a vacuum to remove excess o-xylene and to ultimately purify the target benzaldehyde. The final product was recovered which comprised a substantially pure amount of 3,4-dimethylbenzaldehyde (196.66 g; 1466 mmol). The final yield was calculated to be approximately 95.4% from the starting aluminum chloride material (1466 mmol/1537 mmol=95.4%).

EXAMPLE 2

200 g of aluminum chloride (mol. wt. 133.34; 1500 mmol) and about 730 g of 1,2,3-trimethylbenzene (mol. wt. 120.2; 6073 mmol) were charged to a 2 liter Paar®-brand stainless steel reaction vessel. The vessel was sealed, purged two times with nitrogen at 50 psi, then once with carbon monoxide at a pressure of 100 psi. After the final purging, the vessel was vented and a final introduction of CO was made at a pressure again of about 100 psi, the pressure at which the reaction was maintained for the total reaction time of about 14 hours (the reaction temperature was maintained at −3° C. for the duration as well). Once the reaction was complete, the resultant mixture was poured into about 500 mL of ice water to produce about 900 mL of a two-phase mixture. The top, organic layer was removed and washed three times with water using a separatory funnel and dried over magnesium sulfate. The residual organic phase was then decolorized with activated charcoal and subsequently distilled under a vacuum to remove excess 1,2,3-trimethylbenzene and to ultimately purify the target benzaldehyde. The final product, 2,3,4-trimethylbenzaldehyde, was recovered in an amount of about 222.0 g (about 1124 mmol), for a yield of about 74.9%.

EXAMPLE 3

101.1 g of aluminum chloride (758 mmol) and about 268.8 g of o-xylene (2530 mmol) were charged to a 2 liter Paar®-brand stainless steel reaction vessel. The vessel was sealed, purged three times with carbon monoxide with the pressure of the vessel increased to 90 psi for each purging. After the third time, the vessel was vented and a final introduction of CO was made at a pressure again of about 90 psi, the pressure at which the reaction was maintained for the total reaction time of about 1.5 hours (the reaction temperature was maintained at about 15° C. for the duration as well). Once the reaction was complete, the reaction vessel (and resultant mixtures) was purged two times in a nitrogen atmosphere at 50 psi. The recovered product mixture was then poured into about 500 mL of ice water to produce about 900 mL of a two-phase mixture. The top, organic layer was removed and washed three times with water using a separatory funnel and filtered with sodium carbonate. The residual organic phase was then distilled from the sodium carbonate and was found to be approximately 99% pure 3,4-dimethyl benzaldehyde (by gas chromatograph analysis). The yield was about 80.0 g (596.6 mmol), calculated to be approximately 78.7% from the starting aluminum chloride material.

EXAMPLE 4 (Comparative)

105.4 g of aluminum chloride and about 390 g of chlorotoluene were charged to a 2 liter Paar®-brand reaction vessel. The vessel was sealed, purged three times with carbon monoxide with the pressure of the vessel increased to 90 psi for each purging. After the third time, the vessel was vented and a final introduction of CO was made at a pressure again of about 90 psi, the pressure at which the reaction was maintained for the duration of the reaction which lasted for about 3 days (the reaction temperature was maintained at about 25° C. for the duration as well). Once the reaction was complete, the reaction vessel (and resultant mixtures) was purged two times in a nitrogen atmosphere at 50 psi. The recovered product mixture was then poured into about 500 mL of ice water to produce about 900 mL of a one-phase, homogeneous mixture. This mixture was then tested by NMR and was found solely to consist of the chlorotoluene starting material thereby indicating the lack of reaction by any catalyst to produce a benzaldehyde.

Having described the invention in detail it is obvious that one skilled in the art will be able to make variations and modifications thereto without departing from the scope of the present invention. Accordingly, the scope of the present invention should be determined only by the claims appended hereto.

That which is claimed is:

1. A method of producing a benzaldehyde of the formula (I)

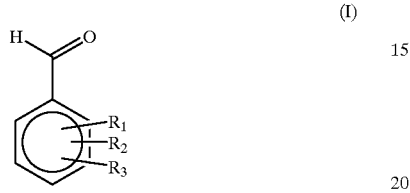

wherein $R^1$, $R^2$, and $R^3$ are the same or different and represent hydrogen and $C_1$–$C_4$ alkyl; and wherein at most one of $R^1$, $R^2$, and $R^3$ is hydrogen; which method is a neat procedure and comprises the reaction between a substituted benzene of the formula (II)

wherein $R^1$, $R^2$, and $R^3$ are the same or different and represent hydrogen and $C_1$–$C_4$ alkyl; and wherein at most one of $R^1$, $R^2$, and $R^3$ is hydrogen, and a carbon monoxide atmosphere having a pressure from about 20 to 200 psig, in the presence of a metal halide and an acid selected from the group consisting of HCl, HBr, HF, HI, and mixtures thereof;

wherein the acid is present in a catalytic amount of from about 0.0001 to about 0.01 moles per moles of the metal halide; and wherein the reaction temperature is from about −20° C. to about 25° C.

2. The method of claim 1 wherein said acid is hydrochloric acid.

3. The method of claim 1 wherein said metal halide is selected from the group consisting of aluminum chloride, aluminum bromide, zirconium chloride, and any mixtures thereof.

4. The method of claim 2 wherein said metal halide is selected from the group consisting of aluminum chloride, aluminum bromide, zirconium chloride, and any mixtures thereof.

5. The method of claim 2 wherein said hydrochloric acid is in aqueous solution.

6. The method of claim 2 wherein said hydrochloric acid is generated within the reaction.

7. The method of claim 2 wherein said temperature is from about −10° to about 5° C. and said hydrochloric acid is added to the reaction.

8. The method of claim 5 wherein said temperature is from about −10° to about 5° C. and said hydrochloric acid is added to the reaction.

9. The method of claim 6 wherein said metal halide is aluminum chloride.

10. The method of claim 7 wherein said temperature is about 0° C. and said metal halide is aluminum chloride.

11. The method of claim 8 wherein said temperature is about 0° C. and said metal halide is aluminum chloride.

12. The method of claim 1 wherein said substituted benzene of Formula (II) is selected from the group consisting of o-xylene, p-xylene, m-xylene, p-diethylbenzene, o-diethylbenzene, m-diethylbenzene, 1,2,3-trimethylbenzene, 1,2,4-trimethylbenzene, 1,2,5-trimethylbenzene, and 1,3,5-trimethylbenzene.

13. The method of claim 2 wherein said substituted benzene of Formula (II) is selected from the group consisting of o-xylene, p-xylene, m-xylene, p-diethylbenzene, o-diethylbenzene, m-diethylbenzene, 1,2,3-trimethylbenzene, 1,2,4-trimethylbenzene, 1,2,5-trimethylbenzene, and 1,3,5-trimethylbenzene.

14. The method of claim 5 wherein said substituted benzene of Formula (II) is selected from the group consisting of o-xylene, p-xylene, m-xylene, p-diethylbenzene, o-diethylbenzene, m-diethylbenzene, 1,2,3-trimethylbenzene, 1,2,4-trimethylbenzene, 1,2,5-trimethylbenzene, and 1,3,5-trimethylbenzene.

15. The method of claim 6 wherein said substituted benzene of Formula (II) is selected from the group consisting of o-xylene, p-xylene, m-xylene, p-diethylbenzene, o-diethylbenzene, m-diethylbenzene, 1,2,3-trimethylbenzene, 1,2,4-trimethylbenzene, 1,2,5-trimethylbenzene, and 1,3,5-trimethylbenzene.

16. The method of claim 9 wherein said substituted benzene of Formula (II) is selected from the group consisting of o-xylene, p-xylene, m-xylene, p-diethylbenzene, o-diethylbenzene, m-diethylbenzene, 1,2,3-trimethylbenzene, 1,2,4-trimethylbenzene, 1,2,5-trimethylbenzene, and 1,3,5-trimethylbenzene.

17. The method of claim 10 wherein said substituted benzene of Formula (II) is selected from the group consisting of o-xylene, p-xylene, m-xylene, p-diethylbenzene, o-diethylbenzene, m-diethylbenzene, 1,2,3-trimethylbenzene, 1,2,4-trimethylbenzene, 1,2,5-trimethylbenzene, and 1,3,5-trimethylbenzene.

18. The method of claim 11 wherein said substituted benzene of Formula (II) is selected from the group consisting of o-xylene, p-xylene, m-xylene, p-diethylbenzene, o-diethylbenzene, m-diethylbenzene, 1,2,3-trimethylbenzene, 1,2,4-trimethylbenzene, 1,2,5-trimethylbenzene, and 1,3,5-trimethylbenzene.

* * * * *